(12) United States Patent
Zaballa et al.

(10) Patent No.: US 10,278,685 B2
(45) Date of Patent: May 7, 2019

(54) ELECTROSPINNING DEVICE AND METHOD FOR APPLYING POLYMER TO TISSUE

(71) Applicant: Covidien LP, Mansfield, MA (US)

(72) Inventors: Vincent Zaballa, Colorado Springs, CO (US); Daniel A. Friedrichs, Aurora, CO (US)

(73) Assignee: Covidien LP, Mansfield, MA (US)

( * ) Notice: Subject to any disclaimer, the term of this patent is extended or adjusted under 35 U.S.C. 154(b) by 546 days.

(21) Appl. No.: 15/072,391

(22) Filed: Mar. 17, 2016

(65) Prior Publication Data

US 2016/0287227 A1 Oct. 6, 2016

Related U.S. Application Data

(60) Provisional application No. 62/141,467, filed on Apr. 1, 2015.

(51) Int. Cl.
*A61B 17/00* (2006.01)
*D01D 5/00* (2006.01)
(Continued)

(52) U.S. Cl.
CPC .... *A61B 17/0057* (2013.01); *A61B 17/00491* (2013.01); *A61M 25/0082* (2013.01);
(Continued)

(58) Field of Classification Search
CPC .......... A61B 17/0057; A61B 17/00491; A61B 2017/00004; A61B 2017/00522;
(Continued)

(56) References Cited

U.S. PATENT DOCUMENTS 6,616,435 B2 9/2003 Lee et al.
6,713,011 B2 3/2004 Chu et al.
(Continued)

FOREIGN PATENT DOCUMENTS

WO 2014118585 A2 8/2014

OTHER PUBLICATIONS

Guen Hyung Kim et al.: "A Direct-Electrospinning Process by Combined Electric Field and Air-Blowing System for Nanofibrous Wound-Dressings", Applied Physics A; Materials Science and Processing, Springer, Berlin, DE, vol. 90, No. 3, Nov. 15, 2007, pp. 389-394.

(Continued)

*Primary Examiner* — Ophelia A Hawthorne

(57) ABSTRACT

An electrosurgical electrospinning device is presented including a reservoir having a polymer solution disposed therein, the reservoir cooperating with a dispensing apparatus configured to dispense the polymer solution from the reservoir. The electrosurgical electrospinning device further includes a plurality of nozzles connected to the reservoir, each nozzle of the plurality of nozzles including a plurality of needles and a blow-spraying mechanism for blowing gas around each nozzle of the plurality of nozzles when the polymer solution is dispensed from the plurality of needles. The gas from the blow-spraying mechanism and the polymer solution from the plurality of needles are coaxially applied directly onto tissue at voltages of less than or equal to 3 kV.

20 Claims, 16 Drawing Sheets

(51) Int. Cl.
*B29C 47/00* (2006.01)
*B29C 47/06* (2006.01)
*A61M 25/00* (2006.01)
*A61F 2/00* (2006.01)
*B29L 31/00* (2006.01)

(52) U.S. Cl.
CPC ...... *B29C 47/0002* (2013.01); *B29C 47/0076* (2013.01); *B29C 47/065* (2013.01); *D01D 5/0069* (2013.01); *D01D 5/0084* (2013.01); *D01D 5/0092* (2013.01); *A61B 2017/00004* (2013.01); *A61B 2017/0065* (2013.01); *A61B 2017/00522* (2013.01); *A61B 2017/00646* (2013.01); *A61B 2017/00659* (2013.01); *A61B 2017/00884* (2013.01); *A61B 2017/00951* (2013.01); *A61F 2002/0072* (2013.01); *B29L 2031/7546* (2013.01)

(58) Field of Classification Search
CPC .. A61B 2017/0065; A61B 2017/00659; A61B 2017/00884; A61B 2017/00951; A61M 25/0082; B29C 47/0002; B29C 47/0076; B29C 47/065; D01D 5/0069; D01D 5/0084; A61F 2002/0072; A61F 13/00085; B29L 2031/7546
See application file for complete search history.

(56) References Cited

U.S. PATENT DOCUMENTS

| | | |
|---|---|---|
| 6,753,454 B1 | 6/2004 | Smith et al. |
| 7,134,857 B2 | 11/2006 | Andrady et al. |
| 7,794,219 B2 | 9/2010 | Dubson et al. |
| 8,088,324 B2 | 1/2012 | Andrady et al. |
| 8,550,798 B2 | 10/2013 | Seo et al. |
| 8,641,960 B1 | 2/2014 | Medeiros et al. |
| 8,992,594 B2 | 3/2015 | Soletti et al. |
| 9,011,754 B2 | 4/2015 | Leong et al. |
| 2005/0073075 A1 | 4/2005 | Chu et al. |
| 2006/0049542 A1 | 3/2006 | Chu et al. |
| 2012/0240369 A1 | 9/2012 | Capparelli Mattoso et al. |
| 2013/0030452 A1 | 1/2013 | Itskovitz-Eldor et al. |
| 2014/0303490 A1 | 10/2014 | Mather et al. |
| 2014/0324078 A1 | 10/2014 | Buschmann |
| 2015/0064142 A1 | 3/2015 | Green et al. |

OTHER PUBLICATIONS

Alessio Varesano et al.: "Multi-Jet Nozzle Electrospinning on Textile Substrates: Observations on Process and Nanofibre Mat Deposition", Polymer International, Barking, GB, Jan. 1, 2010, pp. 1-10.
European Search Report EP16163168 dated Jul. 29, 2016.

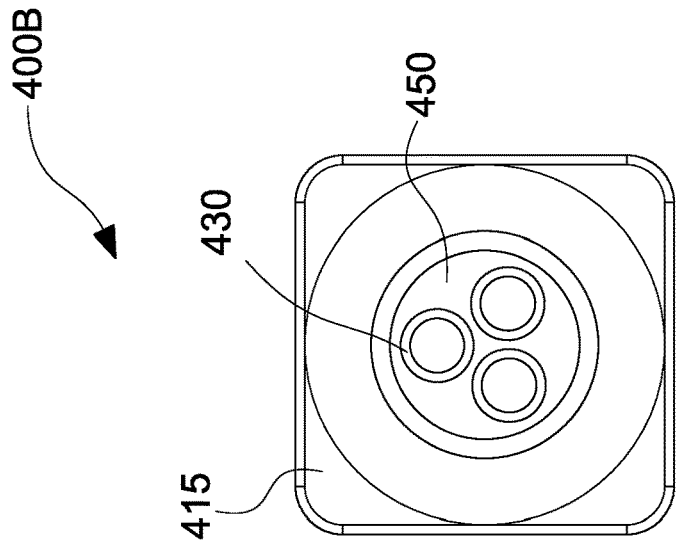
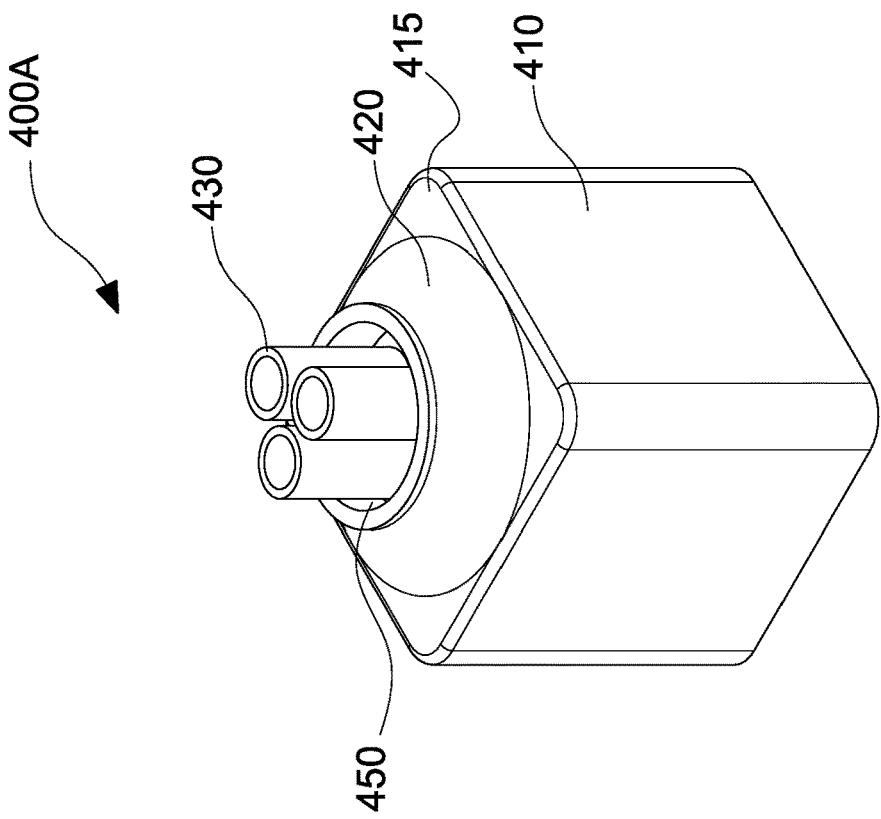
FIG. 4B
FIG. 4A

ELECTROSPINNING DEVICE AND METHOD FOR APPLYING POLYMER TO TISSUE

CROSS-REFERENCE TO RELATED APPLICATIONS

This application claims the benefit of and priority to U.S. Provisional Patent Application No. 62/141,467 filed Apr. 1, 2015, the entire disclosure of which is incorporated by reference herein.

TECHNICAL FIELD

The present disclosure relates to electrospinning. More particularly, the present disclosure relates to a device and method for applying polymer to tissue via a combination of electrospinning and blow-spraying techniques.

BACKGROUND OF RELATED ART

Chronic wounds, ulcers, hernias, and gastrointestinal (GI) perforations are injuries that give patients pain due to openings to an external and foreign environment. These injuries are currently treated by mechanical means, including sutures and meshes, which may not be completely effective at preventing reoccurrence of the injury.

Polymers, such as polyvinyl alcohol (PVA) and polyethylene (PE) are capable of undergoing a process known as electrospinning that excites the polymer solution by contact with a high voltage source (above 2 kV) and secretion through a nozzle, and deposits fibers with diameters in the range of nanometers to a grounded substrate. Electrospinning is a useful process for deposition of fibers to be used as scaffolding for tissue engineering purposes, as the architecture for the deposited nanofibers induces cell migration and healing in vivo and in situ.

Electrospinning is a versatile method for generating very thin fibers made of polymers, ceramics, metals, carbon, and/or composite materials. A somewhat similar technique called electrospray can be used to produce a micro/nanometric jet that breaks up to give rise to an aerosol of charged droplets. Electrospray has a proven ability to generate monodisperse aerosols with sizes ranging from a few nanometers to hundreds of microns. Electrospinning, by contrast, typically generates a jet in a high-voltage field to produce elongated polymeric fibers. Compared with electrospray, which uses electro-hydrodynamic forces to generate a number of particles in an aerosol or a hydrosol phase, electrospinning is a more demanding technique that requires the use of a solution with appropriate viscosity, surface tension, and conductivity to produce continuous liquid jets.

In conventional electrospinning, a suitable polymer solution, or melt, is subjected to a high-voltage electrical field to create an electrically charged jet that creates a solid fiber that has removed most of the solvent from the solution, but has not completely removed the solvent and created a 'dry' fiber. For example, one electrode from a high-voltage source may be placed into a polymer solution and the other attached to a conductive collector, such as a panel of aluminum foil or a silicon wafer. A typical apparatus for electrospinning utilizes a spinneret with a metallic needle, a syringe pump providing the working fluid to the spinneret, a high-voltage power supply, and a grounded collector. A polymer, sol-gel, or composite solution or melt is loaded into the syringe pump, and this viscous liquid is driven to the needle tip, forming a droplet at the tip. When a voltage is applied to the metallic needle, the droplet is first stretched into a structure called a Taylor cone and, finally, into an electrified jet. The jet is then elongated and whipped continuously by electrostatic repulsion until it is deposited on the grounded collector. The elongation by bending instability results in the formation of uniform fibers that may typically have nanometer-scale diameters.

Also disclosed herein is an electrospinning process for the production of various-sized nanofibers.

SUMMARY

The present disclosure relates to a handheld electrosurgical electrospinning device. The handheld electrosurgical electrospinning device includes a reservoir having a polymer solution disposed therein. The reservoir cooperates with a dispensing apparatus that is configured to dispense the polymer solution from the reservoir. The electrospinning device also has a plurality of nozzles connected to the reservoir and each nozzle of the plurality of nozzles includes a plurality of needles. A blow-spraying mechanism is included for blowing gas around each nozzle of the plurality of nozzles when the polymer solution is dispensed from the plurality of needles. The gas from the blow-spraying mechanism and the polymer solution from the plurality of needles are coaxially applied directly onto tissue at voltages of less than or equal to 3 kV.

In disclosed embodiments, the reservoir may be a syringe and the dispensing apparatus may be a syringe pump.

In disclosed embodiments, the plurality of nozzles are arranged in a linear configuration. In an alternative embodiment, the plurality of nozzles are arranged in a circular configuration. In yet another alternative embodiment, the plurality of nozzles are arranged as an array.

In disclosed embodiments, the electrospinning device operates at a voltage approximately between 2 kV and 2.98 kV.

In disclosed embodiments, the plurality of nozzles deposit a mixture of nano-scale and large-scale fibers onto tissue.

In disclosed embodiments, a deposition distance of the nano-scale and large-scale fibers is approximately between 25 mm and 100 mm.

In disclosed embodiments, the electrosurgical electrospinning device is a handheld device including a shaft connected to a handle portion at a proximal end thereof, the shaft incorporating the electrosurgical electrospinning device at a distal end thereof.

In disclosed embodiments, the electrospinning device includes a flexible catheter connected to a body portion and also includes the flexible catheter including the plurality of nozzles therein.

In disclosed embodiments, the flexible catheter includes a proximal end and a distal end, and the plurality of nozzles are positioned a predetermined distance away from the distal end of the flexible catheter, thus creating a space between the distal end of the catheter and the plurality of nozzles. The predetermined distance may be between approximately 8 mm and 15 mm.

In disclosed embodiments, the plurality of nozzles are configured to be repositioned within the flexible catheter to adjust a distance between the plurality of nozzles and a distal end of the flexible catheter. The distance adjustment may be between approximately 8 mm and 15 mm.

The present disclosure also relates to an electrosurgical electrospinning method performed by an electrosurgical electrospinning device. The method includes dispensing polymer solution from a reservoir via a dispensing apparatus, connecting a plurality of nozzles to the reservoir, each nozzle of the plurality of nozzles including a plurality of needles, and blowing gas, via a blow-spraying mechanism, around each nozzle of the plurality of nozzles when the polymer solution is dispensed from the plurality of needles. The method further includes the step of coaxially applying the gas from the blow-spraying mechanism and the polymer solution from the plurality of needles directly onto tissue at voltages of less than or equal to 3 kV.

BRIEF DESCRIPTION OF THE DRAWINGS

The above and other aspects, features, and advantages of the present disclosure will become more apparent in light of the following detailed description when taken in conjunction with the accompanying drawings in which:

FIG. 4A is a perspective view of a coaxial nozzle having 3 electrospinning needles in a substantially circular configuration, in accordance with the embodiments of the present disclosure;

FIG. 4B is a top view of the coaxial nozzle of FIG. 4A having 3 electrospinning needles in a substantially circular configuration, in accordance with the embodiments of the present disclosure;

DETAILED DESCRIPTION

Figure 1:
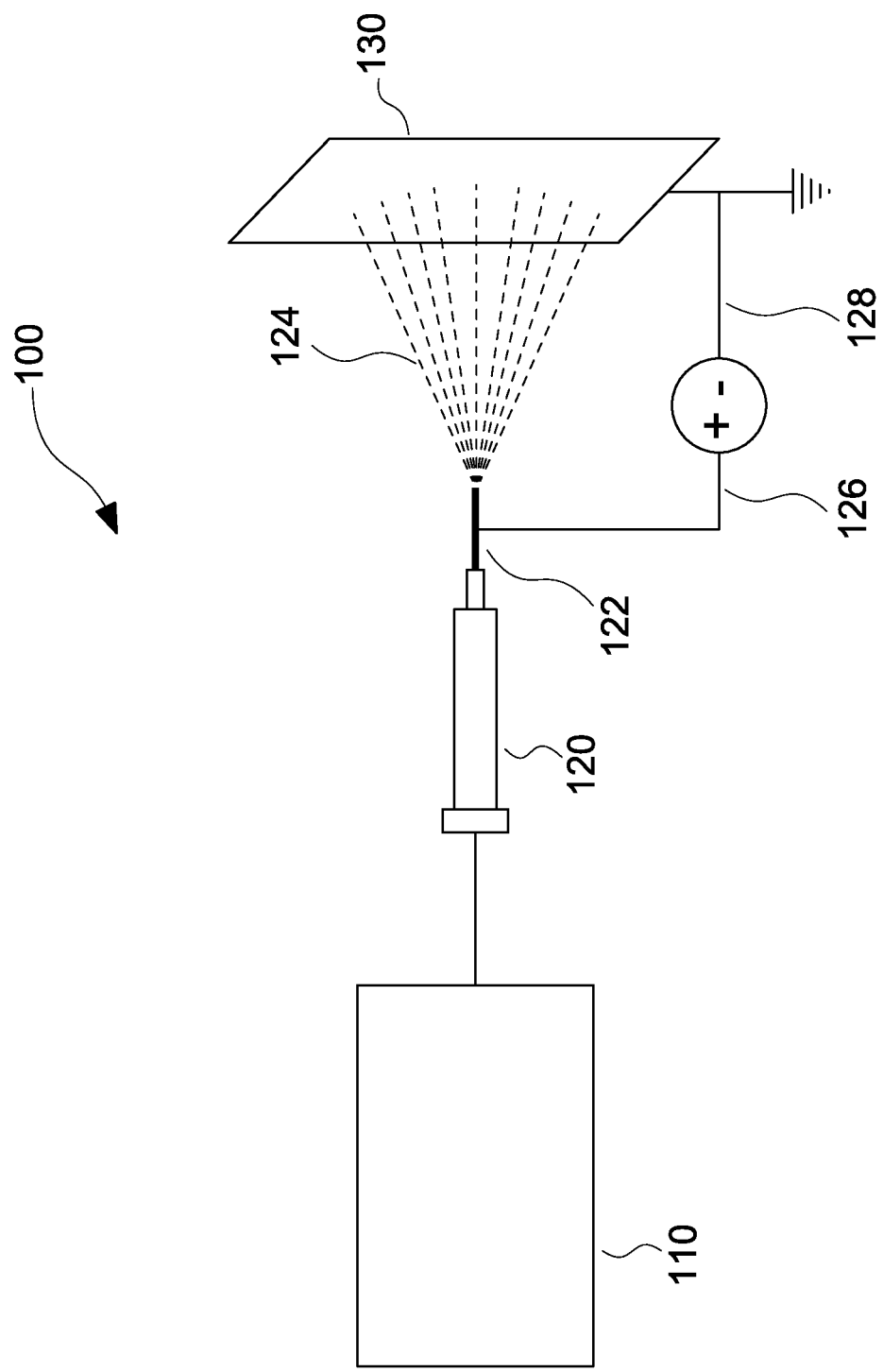
FIG. 1 is a schematic representation of an electrospinning system.

Currently, electrospinning has only been used in vitro in biomedical applications to create scaffolds for tissue engineering purposes. However, the exemplary embodiments of the present disclosure describe a device that would electrospin at a modest voltage level (approximately the same voltage as electrosurgery) and deposit enough polymer droplets and fibers to substantively treat hernias and other tissue defects.

Particular embodiments of the present disclosure are described hereinbelow with reference to the accompanying drawings. However, it is to be understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure. Like reference numerals refer to similar or identical elements throughout the description of the figures.

As used herein, the term "distal" refers to that portion of the instrument, or component thereof which is farther from the user while the term "proximal" refers to that portion of the instrument or component thereof which is closer to the user.

Various embodiments of the electrospinning device disclosed herein may be employed in endoscopic, laparoscopic, open surgical procedures, interventional and/or intralumenal procedures such as gastrointestinal (GI) sheathing (metabolic/bariatric) and/or banding, and/or for more advanced minimally invasive procedures such as those which employ a device that facilitates multiple instrument access through a single opening and permits a user to operate through a single entry point, i.e., navel, vagina and/or anus.

Reference will now be made in detail to embodiments of the present disclosure. While certain exemplary embodiments of the present disclosure will be described, it will be understood that it is not intended to limit the embodiments of the present disclosure to those described embodiments. To the contrary, reference to embodiments of the present disclosure is intended to cover alternatives, modifications, and equivalents as may be included within the spirit and scope of the embodiments of the present disclosure as defined by the appended claims.

With reference to FIG. 1, an electrospinning system 100 is presented. The electrospinning system 100 includes a reservoir 120 connected to a dispensing apparatus 110 at a proximal end thereof. The distal end of the reservoir 120 includes a needle 122. The needle 122 is a metal needle. The needle 122 is connected to a positive lead 126. Polymer or polymer solution 124 is ejected or dispensed from the needle 122 and received on a substrate 130. The polymer solution 124 is dispensed under pressure that is generated by a pump, described below. The substrate 130 is connected to a ground lead 128. The reservoir 120 may be a syringe, whereas the dispensing apparatus 110 may be a syringe pump.

In operation, bench top electrospinning involves inserting the polymer solution 124 of choice into the reservoir 120 with the needle 122, coupling the reservoir 120 with the dispensing apparatus 110, attaching a positive voltage lead 126 to the needle 122 of the reservoir 120, and a ground lead 128 to the substrate 130 where the material is deposited. The voltage is then turned on. Once the polymer solution 124 within the needle 122 is excited enough, it forms a "cone" that produces a "jet" of polymer, which travels along an electric field created between the positive lead 126 and the grounded substrate 130, as described below with reference to FIG. 2.

Alternatively, instead of a substrate 130, the polymer solution 124 may be directly deposited on tissue of a patient at low voltages in the far field regime. The patient is connected to ground whether the procedure is a monopolar or bipolar electrosurgical procedure. In monopolar electrosurgery, a source or active electrode delivers RF energy from an electrosurgical generator to tissue and a return electrode (e.g., a return pad) carries the current back to the generator. In monopolar electrosurgery, the active electrode is typically part of the surgical instrument held by the surgeon and applied to tissue to be treated. The patient return electrode is placed remotely from the active electrode to carry the current back to the generator. In bipolar electrosurgery, one of the electrodes of the hand-held instrument functions as the active electrode and the other as the return electrode. The return electrode is placed in close proximity to the active electrode such that an electrical circuit is formed between the two electrodes (e.g., electrosurgical forceps). In this manner, the applied electrical current is limited to the body tissue positioned between the electrodes. When the electrodes are sufficiently separated from one another, the electrical circuit is open and thus inadvertent contact of body tissue with either of the separated electrodes does not cause current to flow.

Figure 2:
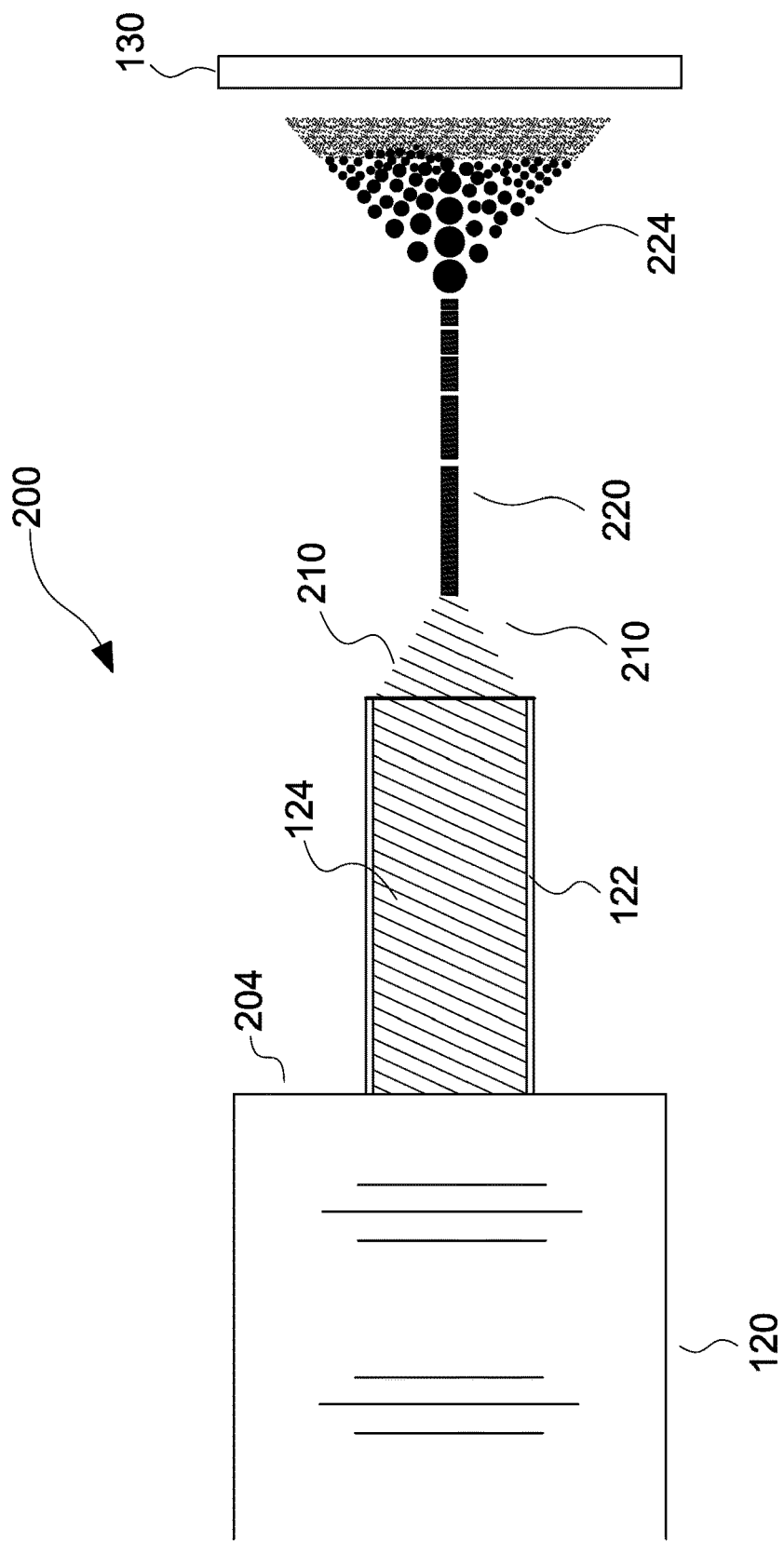
FIG. 2 is a cone and jet produced by the electrospinning system of FIG. 1.

With reference to FIG. 2, a cone 210 and jet 220 are produced by the electrospinning system 100 of FIG. 1. The dispensement mechanism 200 illustrates reservoir 120 having the needle 122 at a distal end 204 thereof. When polymer solution 124 is pumped through the reservoir 120, the polymer solution 124 is dispensed from the needle 122 forming a cone 210 that produces a jet of polymer 220. The jet of polymer 220 travels in an electric field created between the positive lead 126 and the negative or ground lead 128 (see FIG. 1). After travelling a certain distance, the polymer solution 124 becomes a plume 224 that is received by the substrate 130. The plume 224 is dependent on the distance of the needle 122 from the substrate 130, as well as dependent on the voltage difference between the positive lead 126 and the negative lead 128. The cone 210 may be referred to as a Taylor cone, whereas the jet of polymer 220 may be referred to as a Taylor jet.

Figure 3A:
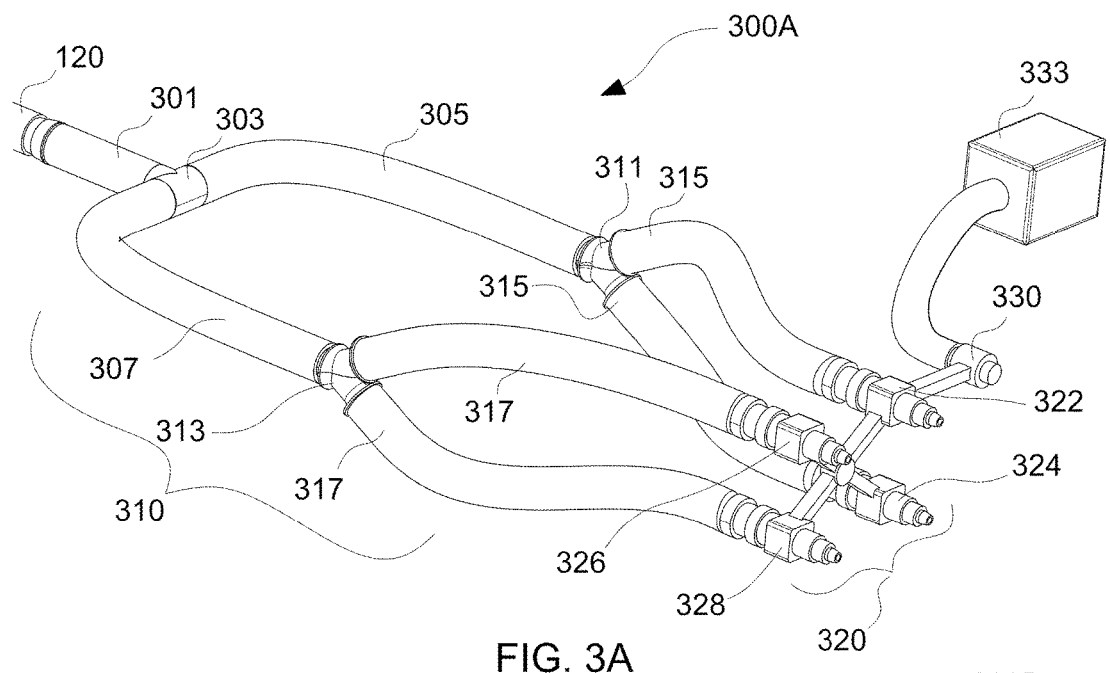
FIG. 3A is a perspective view of the electrospinning device having blow-spraying capabilities, in accordance with the embodiments of the present disclosure.
Figure 3B:
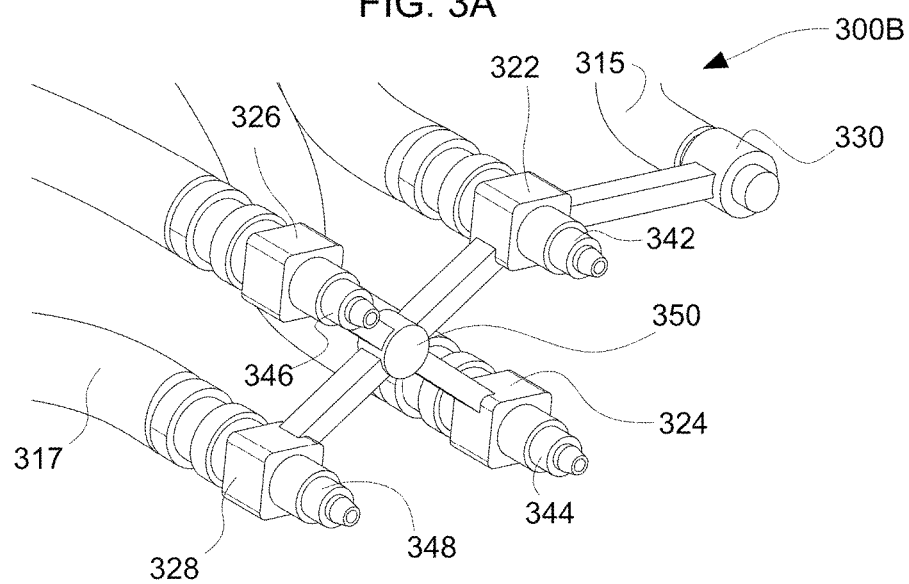
FIG. 3B is an enlarged view of the plurality of nozzles having the plurality of needles of the electrospinning device of FIG. 3A, in accordance with the embodiments of the present disclosure.
Figure 3C:
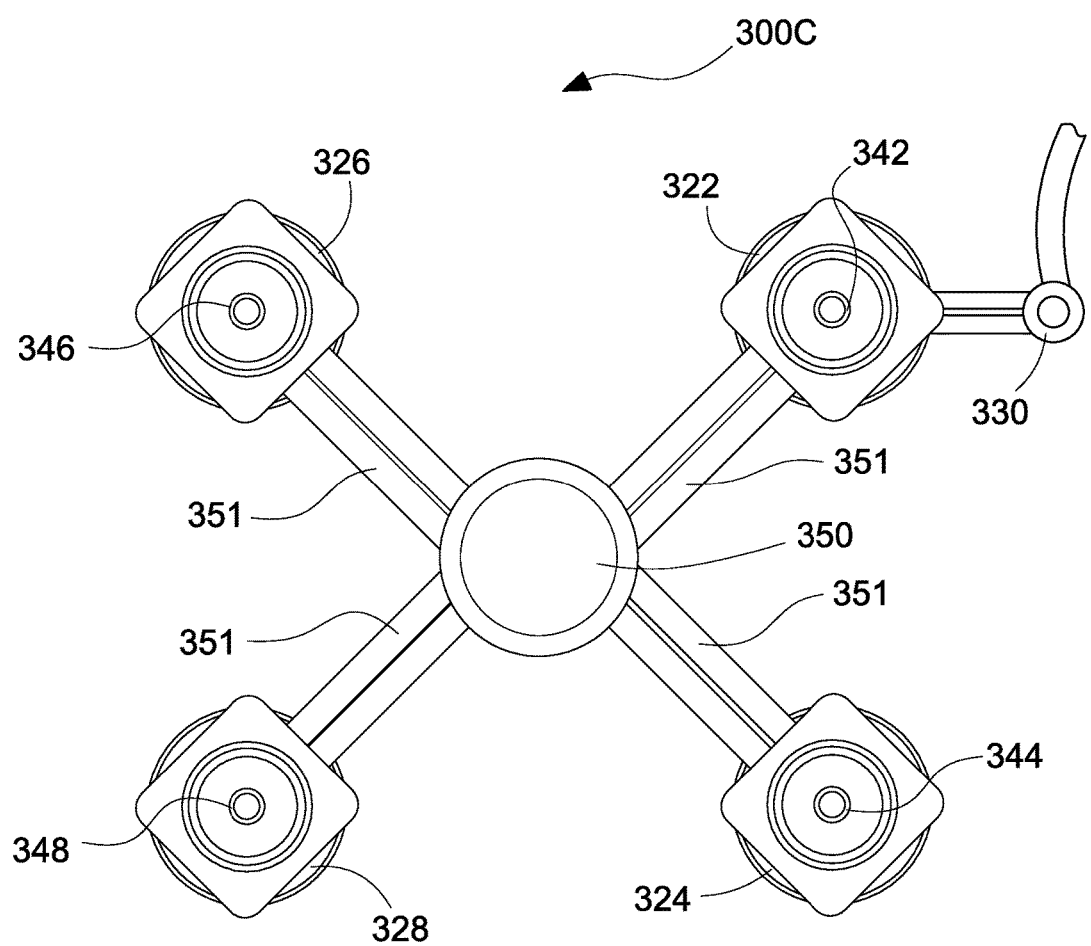
FIGS. 3C and 3D are front views of the plurality of nozzles having one or more needles of the electrospinning device of FIG. 3A, in accordance with the embodiments of the present disclosure.

There are two classes of electrospinning: far-field, which operates in the range of 10 kV and above, and near-field, which operates below 10 kV. In order for the electrospinning device 100 to be safe and clinically relevant, the electrospinning device 100 is operated in a range where arcing does not occur because the electrospinning device 100 is too close to the patient, but also not so far away so that electrospinning does not occur, as distance is a factor for electrospinning. For example, a range of approximately 2 kV to 3 kV may be used. Approximately 2 kV may be the minimum needed to excite the polymer solution 124, whereas approximately 3 kV may be the maximum for regulatory compliance. In certain exemplary embodiments a voltage of approximately 2.1 kV or a voltage 2.5 kV or a voltage of 2.75 kV or a voltage of 2.98 kV is used. Of course, one skilled in the art may contemplate any specific voltage between approximately 2 kV and 3 kV to be used. Additionally, it is contemplated to use voltages between approximately 1 kV and 2 kV. FIGS. 3A-3C achieve such requirements where arcing does not occur, as described below.

With reference to FIG. 3A, a perspective view of the electrospinning device 300A having blow-spraying capabilities is presented, in accordance with the embodiments of the present disclosure.

The electrospinning device 300A includes the reservoir 120 connected to a plurality of nozzles 320. The reservoir 120 is connected to a multi-nozzle configuration 320 via a conduit configuration 310. The conduit configuration 310 may also be referred to as a tubing configuration having a plurality of tubes or tube structures. The tubes may be pipes, ducts, channels or hoses.

The reservoir 120 is connected to a first conduit 301. The first conduit 301 is attached to a T-shaped connector 303. The T-shaped connector 303 is then engaged to a second conduit 305 and a third conduit 307. In turn, the second conduit 305 is connected to two conduits 315 via Y-shaped connector 311, whereas the third conduit 307 is connected to two conduits 317 via Y-shaped connector 313. The distal end of conduits 315 are connected to a first nozzle 322 and a second nozzle 324. The distal end of conduits 317 are connected to a third nozzle 326 and a fourth nozzle 328. The first, second, third, and fourth nozzles 322, 324, 326, 328 are connected to each other via a connector 350 (see FIG. 3B) having a plurality of connecting legs 351 (see FIGS. 3C and 3D). The first, second, third, and fourth nozzles 322, 324, 326, 328 are arranged in a substantially rectangular configuration. However, one skilled in the art may contemplate other configurations, such as linear and arrayed configurations. The connector 350 also includes an air flow or gas flow inlet 330. The gas flow inlet 330 is connected to an air pump 333.

With reference to FIG. 3B, an enlarged view 300B of the multi-nozzle configuration 320 having the plurality of needles of the electrospinning device 300A of FIG. 3A is presented, in accordance with the embodiments of the present disclosure.

The enlarged view 300B illustrates that the first nozzle 322 includes a first needle 342, the second nozzle 324 includes a second needle 344, the third nozzle 326 includes a third needle 346, and the fourth nozzle 328 includes a fourth needle 348. Of course, one skilled in the art may contemplate that each nozzle 322, 324, 326, 328 includes a plurality of needles arranged in different configurations (e.g., circular, rectangular, linear, etc.).

In operation, the multi-nozzle configuration 320 allows polymer solution 124 (see FIGS. 1 and 2) to be pushed out of a plurality of needles 342, 344, 346, 348. Then, a mechanism is presented that allows the electrospinning device 300A to electro-spin at safe distances. This mechanism works by blowing air via the air pump 333 around each of the nozzles 322, 324, 326, 328 where the polymer solution 124 is ejected from and directing the jet 220 created from electrospinning to travel further than allowed by electromagnetic force from the electric field. The legs 351 have internal passages (now shown) for communicating air from air pump 333 to each nozzle 322, 324, 326, 328. Thus, by combining the pressure generated by the dispensing apparatus 110 with the gas pressure and flow generated by the air pump 333 at each nozzle 322, 324, 326, 328, the combinations allows a low voltage to be used without sacrificing the range of the resultant output. The lower voltage with air dispensement allows for far-field range operation. Thus, an assembly that combines both of these aspects for electrospinning is shown in FIGS. 3A and 3B. The coaxial electrospinning device operates at low-voltages. Low-voltage devices are typically only capable of operating in the near-field regime, but the risk of arcing causing patient injury would be unacceptable. However, through the addition of the coaxial design element, the risk of arcing is mitigated, thus allowing low-voltage electrospinning to occur in the far-field regime. Additionally, the electrospinning device 300A is used for depositing polymer fibers and droplets onto tissue (see FIG. 5).

Figure 3D:
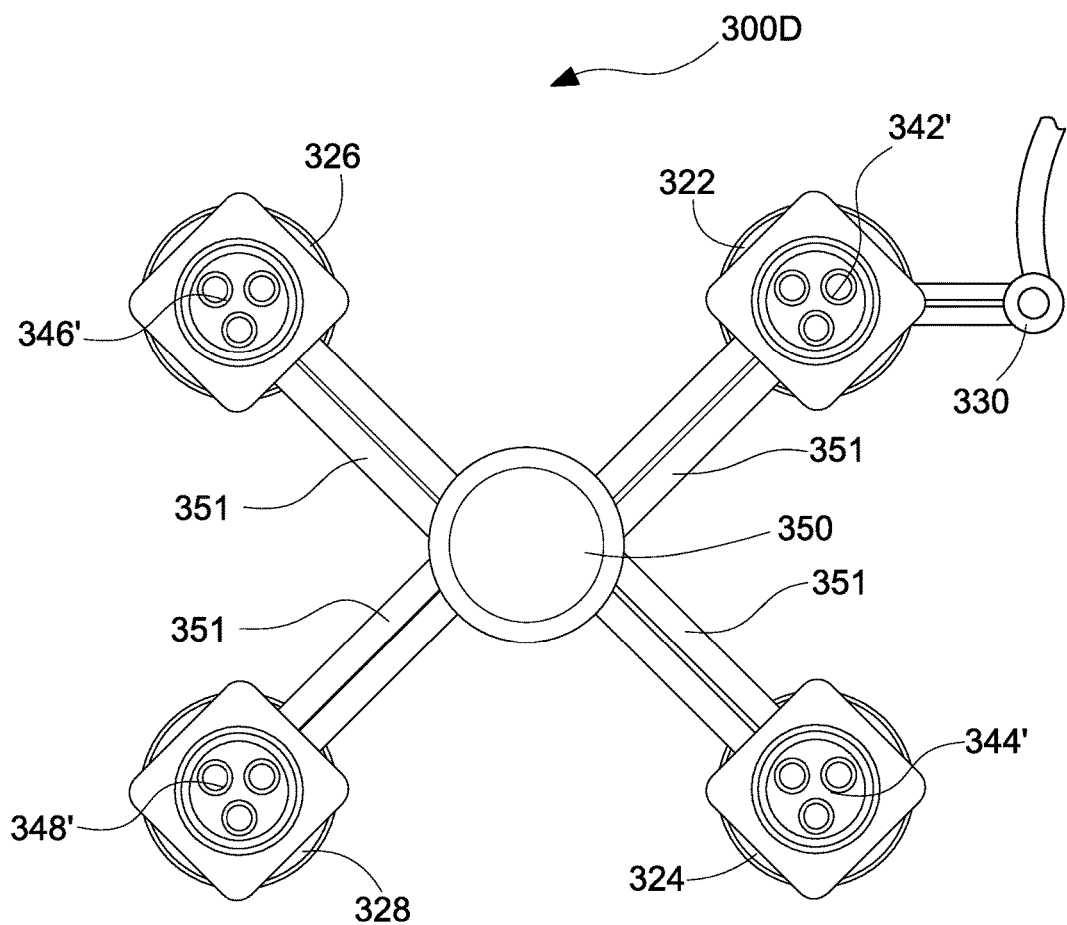

With reference to FIGS. 3C and 3D, front views 300C, 300D of the plurality of nozzles 322, 324, 326, 328 having the plurality of needles of the electrospinning device 300A of FIG. 3A is presented, in accordance with the embodiments of the present disclosure.

The front view 300C illustrates the plurality of nozzles 322, 324, 326, 328 connected to each other via the connector 350 having a plurality of connecting legs 351. First nozzle 322 has a first needle 342, second nozzle 324 has a second needle 344, third nozzle 326 has a third needle 346, and fourth nozzle 328 has a fourth needle 348. Of course, one skilled in the art may contemplate each nozzle having a plurality of needles, as shown in FIG. 3D. For example, first nozzle 322 has a first needle configuration 342', second nozzle 324 has a second needle configuration 344', third nozzle 326 has a third needle configuration 346', and fourth nozzle 328 has a fourth needle configuration 348'.

With reference to FIG. 4A, a perspective view 400A of a coaxial nozzle having 3 electrospinning needles 430 in a substantially circular configuration is presented, in accordance with the embodiments of the present disclosure. With reference to FIG. 4B, a top view 400B of the coaxial nozzle of FIG. 4A having 3 electrospinning needles 430 in a substantially circular configuration is presented, in accordance with the embodiments of the present disclosure.

The perspective view 400A depicts a nozzle body 410 having a tapered nozzle portion 420 on a top portion 415 thereof. The tapered nozzle portion 420 includes a gap 450 through which needles 430 pass through. The top view 400B illustrates the needles 430 in a substantially circular configuration and the gap 450 through which air is blown through when polymer solution is ejected from the needles 430, which will be described in detail below.

Figure 4D:
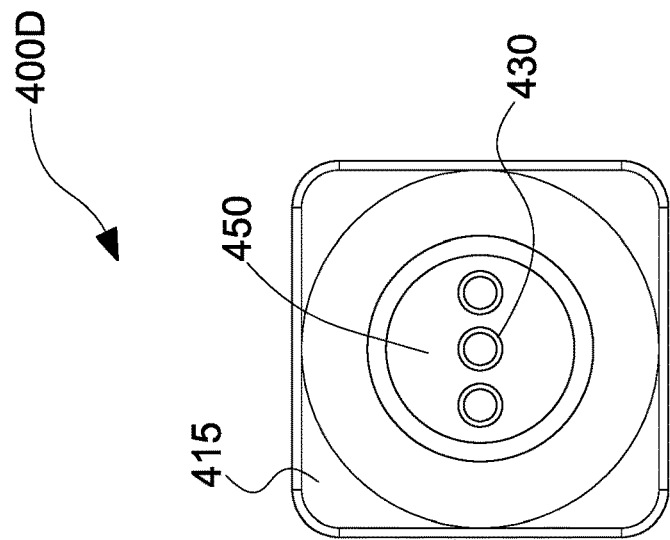
FIG. 4D is a top view of the coaxial nozzle of FIG. 4C having 3 electrospinning needles in a substantially linear configuration, in accordance with the embodiments of the present disclosure.
Figure 4C:
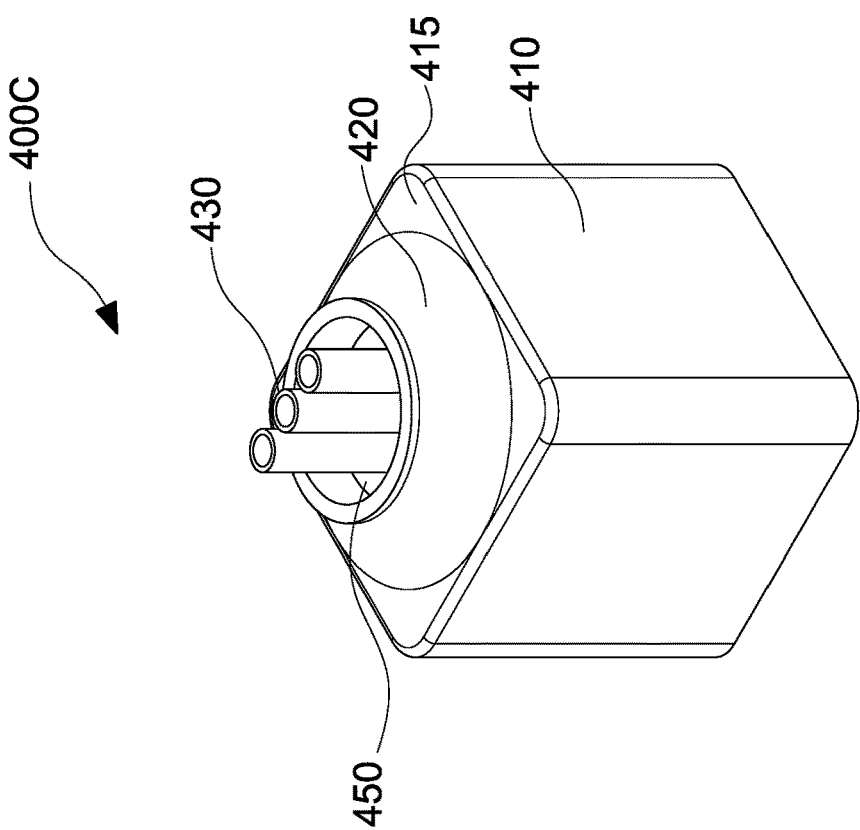
FIG. 4C is a perspective view of a coaxial nozzle having 3 electrospinning needles in a substantially linear configuration, in accordance with the embodiments of the present disclosure.

With reference to FIG. 4C, a perspective view 400C of a coaxial nozzle having 3 electrospinning needles 430 in a substantially linear configuration is presented, in accordance with the embodiments of the present disclosure. With reference to FIG. 4D, a top view 400D of the coaxial nozzle of FIG. 4C having 3 electrospinning needles 430 in a substantially linear configuration is presented, in accordance with the embodiments of the present disclosure.

The perspective view 400C depicts a nozzle body 410 having a tapered nozzle portion 420 on a top portion 415 thereof. The tapered nozzle portion 420 includes a gap 450 through which needles 430 pass through. The top view 400D illustrates the needles 430 in a substantially linear configuration and the gap 450 through which air is blown through when polymer solution is ejected from the needles 430, which will be described in detail below.

Figure 4F:
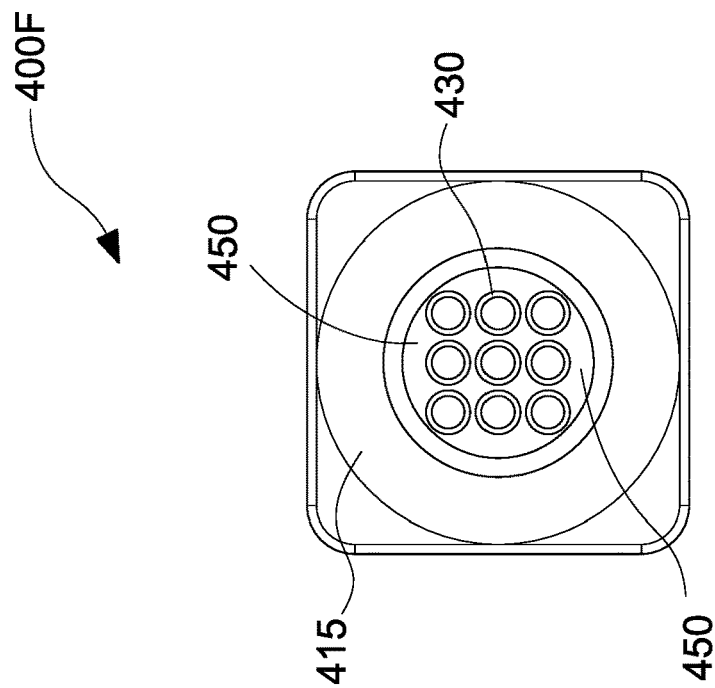
FIG. 4F is a top view of the coaxial nozzle of FIG. 4E having 9 electrospinning needles arranged in an array, in accordance with the embodiments of the present disclosure.
Figure 4E:
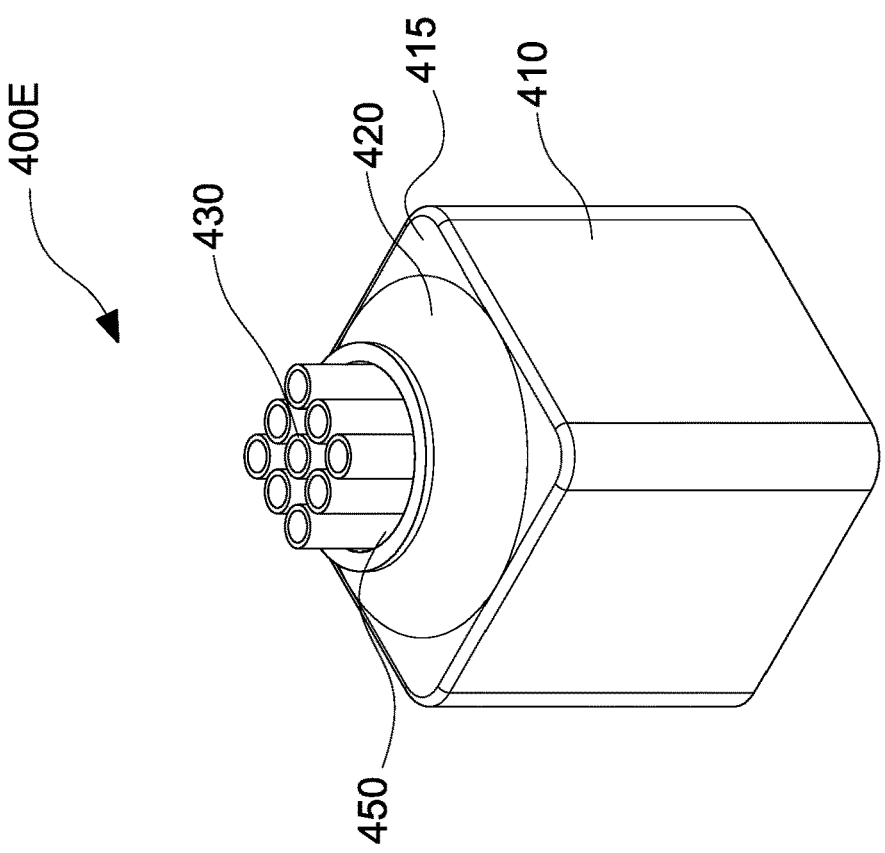
FIG. 4E is a perspective view of a coaxial nozzle having 9 electrospinning needles arranged in an array, in accordance with the embodiments of the present disclosure.

With reference to FIG. 4E, a perspective view 400E of a coaxial nozzle having 9 electrospinning needles arranged in an array is presented, in accordance with the embodiments of the present disclosure. With reference to FIG. 4F, a top view 400F of the coaxial nozzle of FIG. 4E having 9 electrospinning needles arranged in an array is presented, in accordance with the embodiments of the present disclosure.

The perspective view 400E depicts a nozzle body 410 having a tapered nozzle portion 420 on a top portion 415 thereof. The tapered nozzle portion 420 includes a gap 450 through which needle assemblies 430 pass. The top view 400F illustrates the needle assemblies 430 in a array and the gap 450 through which air is blown through when polymer solution is ejected from the needle assemblies 430, which will be described in detail below.

In FIGS. 3A-4F, the needles may be substantially parallel to each other.

Figure 5:
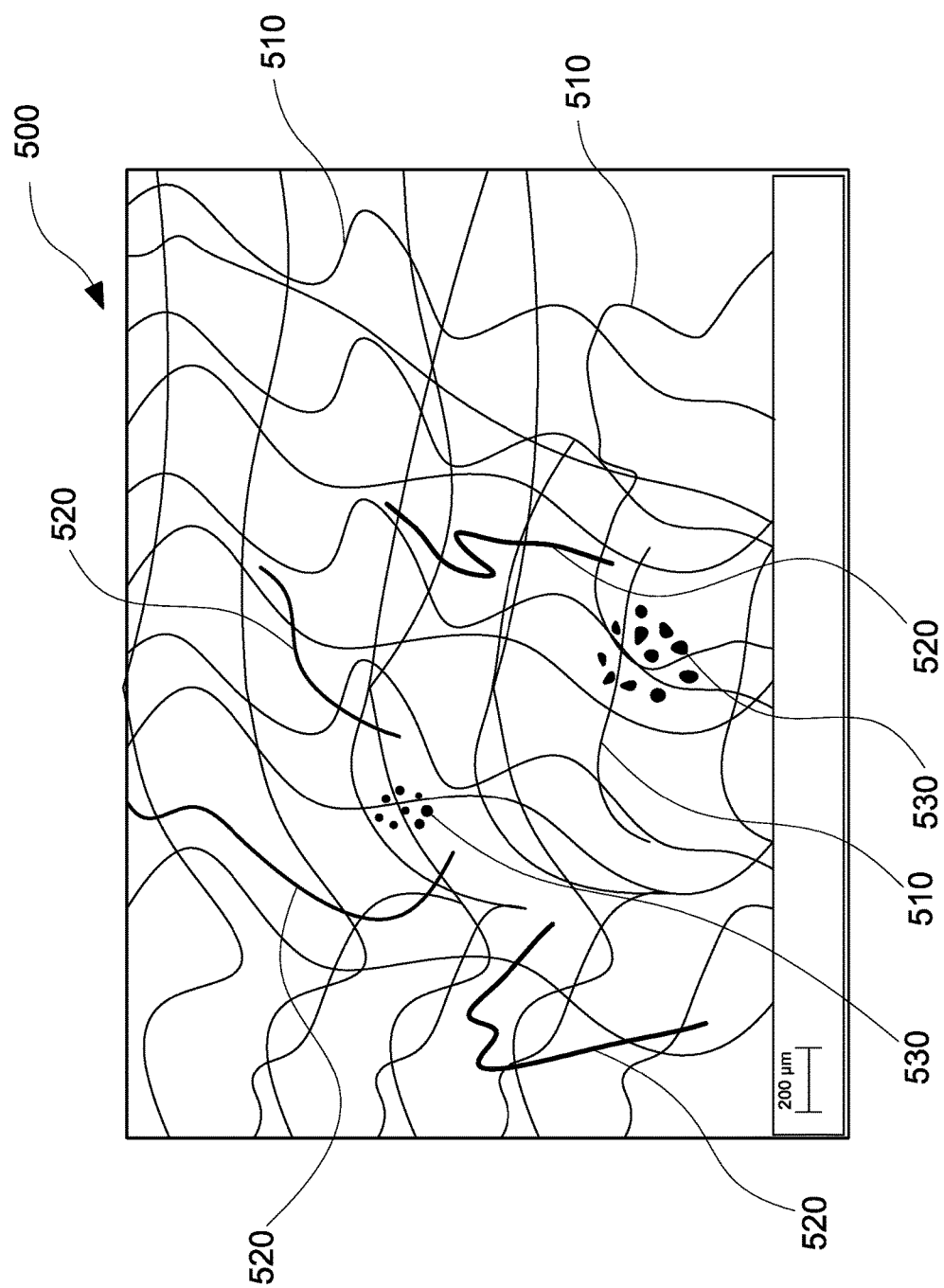
FIG. 5 illustrates a scanning electron microscope image of polymer fibers deposited by the electrospinning device of FIG. 3A, in accordance with the embodiments of the present disclosure.

With reference to FIG. 5, a scanning electron microscope image 500 of polymer fibers 510, 520 and droplets 530 deposited by the electrospinning device 300A of FIG. 3A is presented, in accordance with the embodiments of the present disclosure.

This polymer solution 124 (see FIGS. 1 and 2) is ejected from the needles of the nozzles and are attenuated or stretched to form elongated adhesive fibers 510 and such fibers 510 are imparted with a twisting motion for deposition in a spiral pattern upon the substrate 130 (see FIG. 1). The fibers may be thin fibers 510 or may be thicker fibers 520. Additionally, polymer droplets 530 may be deposited onto substrate 130. Therefore, a mixture of nano-scale fibers 510, large scale fibers 520, and droplet fibers 530 may be achieved through the use of multiple needles and the use of different deposition rates in order to perform in situ deposition for repair of chronic wounds and/or hernia defects. The large scale fibers may be in the micrometer range. For example, the large scale fibers may have a diameter between approximately 1 µm and 20 µm. In another exemplary embodiment, the large scale fibers may have a diameter between approximately 20 µm and 200 µm.

Figure 6A:
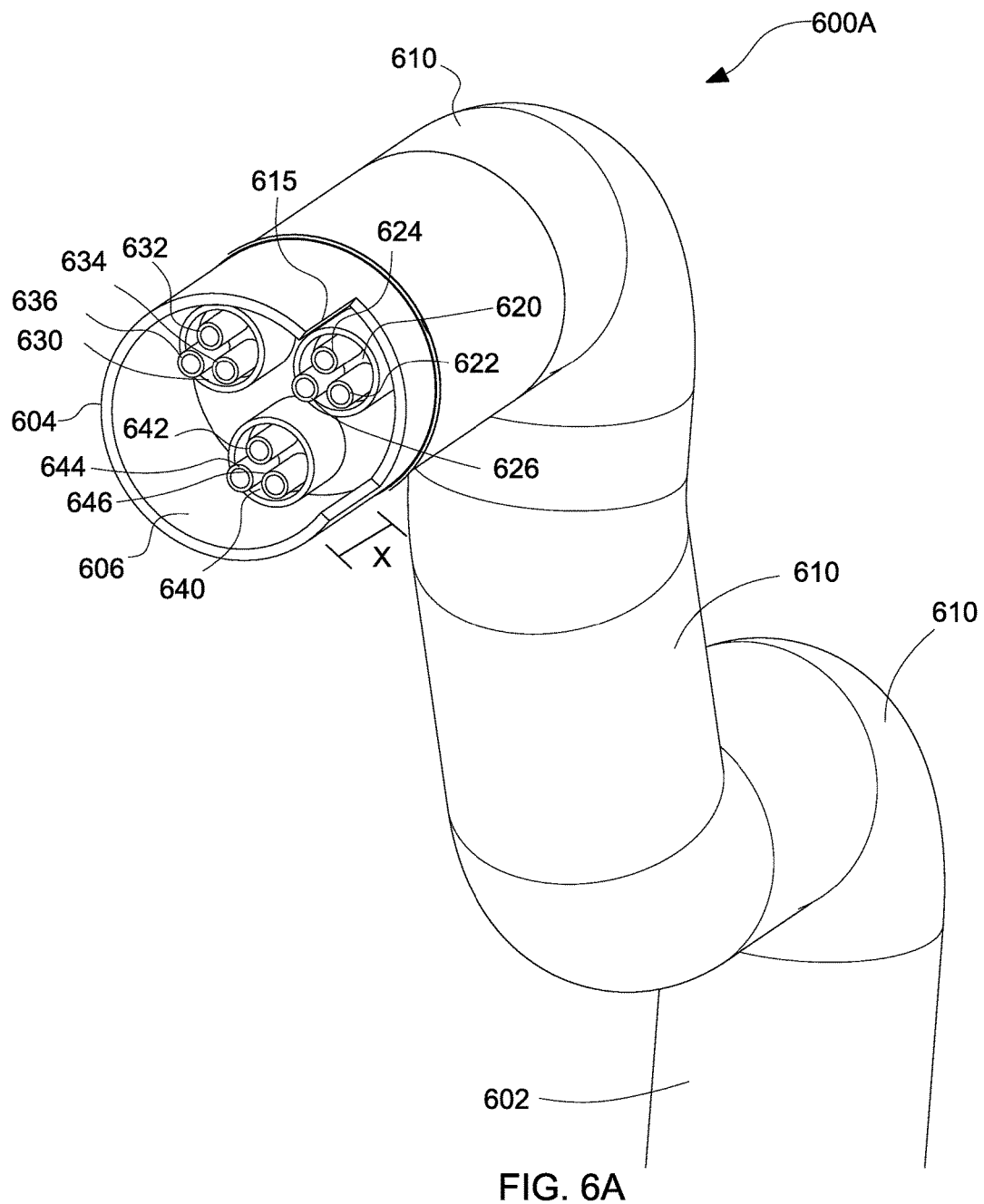
FIG. 6A illustrates a catheter incorporating an electrospinning device, in accordance with the embodiments of the present disclosure.

With reference to FIG. 6A, a catheter 600A is illustrated incorporating an electrospinning device, in accordance with the embodiments of the present disclosure.

The catheter 600A includes a flexible shaft 610. The flexible shaft 610 has a proximal end 602 and a distal end 604. The distal end 604 includes an electrospinning device having 3 nozzles 620, 630, 640. The first nozzle 620 includes 3 needles 622, 624, 626. The second nozzle 630 includes 3 needles 632, 634, 636. The third nozzle includes 640 includes 3 needles 642, 644, 646. A space 606 is illustrated between the distal end 604 of the tip of the catheter 600A and the distalmost end of the nozzles 620, 630, 640 via a cut-away 615. The space 606 eliminates the risk of electrical arcing between the needles and the patient. The distance "X" between the distal end 604 of the tip of the catheter 600A and the distalmost end of the nozzles 620, 630, 640 may be approximately 12 mm. In another embodiment, the distance "X" may be 15 mm. The distance may be varied based on applied voltage. Of course one skilled in the art may contemplate positioning the plurality of nozzles at any suitable distance with respect to the distal end of the catheter 600A.

Figure 6B:
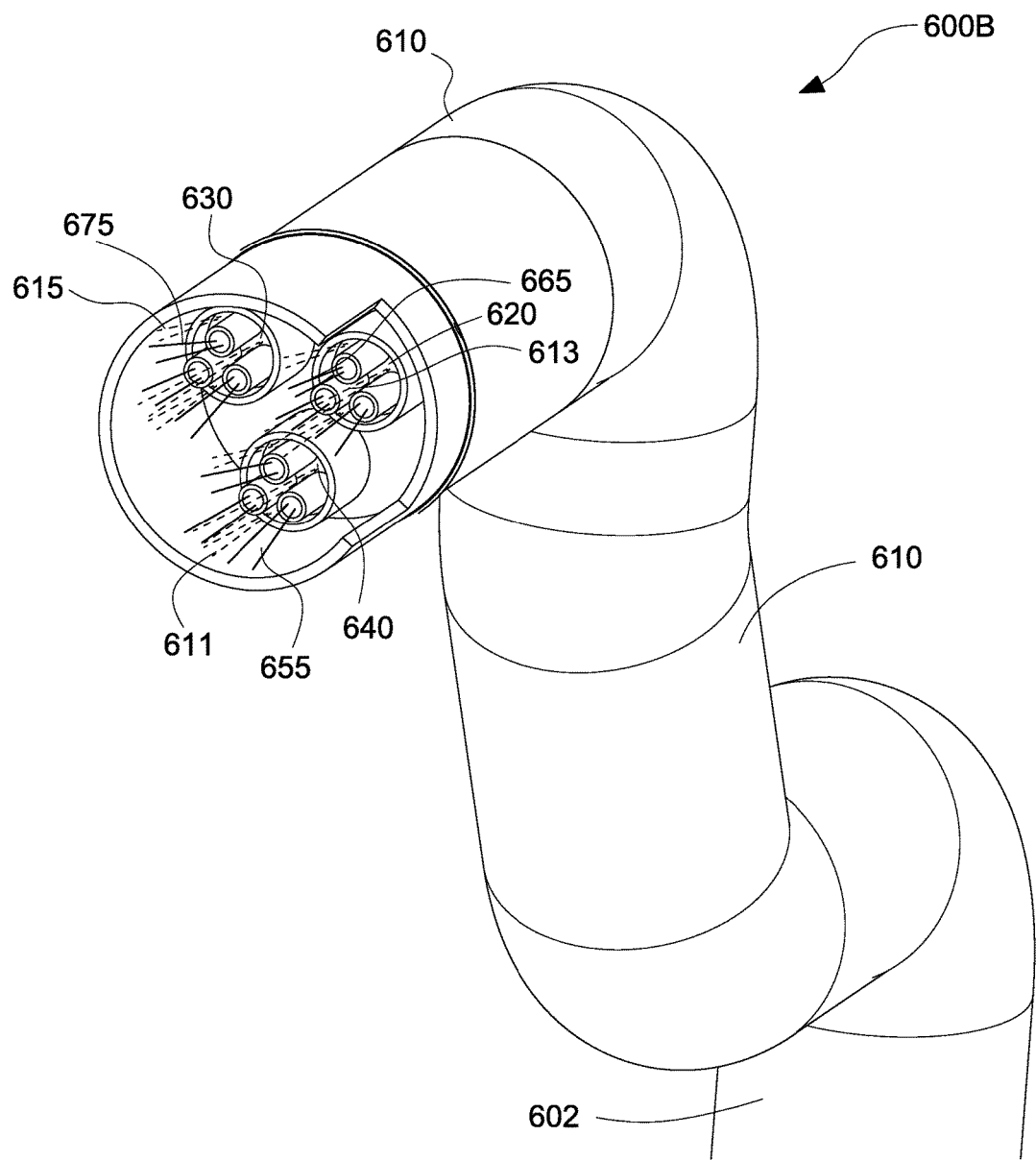
FIG. 6B illustrates the catheter incorporating the electrospinning device in an active state, where coaxial dispensement of gas and polymer solution is enabled, in accordance with the embodiments of the present disclosure.

With reference to FIG. 6B, the catheter 600A of FIG. 6A is illustrated incorporating the electrospinning device in an active state 600B, where coaxial dispensement of gas and polymer solution is enabled, in accordance with the embodiments of the present disclosure.

In the active state 600B, the plurality of nozzles 620, 630, 640 are triggered to dispense polymer solution 655, 665, 675 via their respective needles. The polymer solution 655, 665, 675 is dispensed in jet form followed by a plume. The polymer solution 655, 665, 675 is further propelled by the air or gas 611, 613, 615 dispensed from openings or gaps 650, 660, 670 of nozzles 620, 630, 640, respectively. Therefore, in the active state, the polymer solution 655, 665, 675 is propelled by an electrospinning process, as well as a blow-spraying process. In order to increase polymer solution deposition rates, blow-spraying is combined with electrospinning in a coaxial multi-needle configuration. The addition of blow-spraying by air or gas 611, 613, 615 allows for the generation of larger fibers 520 (see FIG. 5), as well as an increase of the deposition rate. Therefore, a mixture of fibers 510, 520 may be deposited at a fast rate onto a substrate 130 or tissue of a patient. The deposition distance is approximately between 25 mm and 100 mm.

Figure 7:
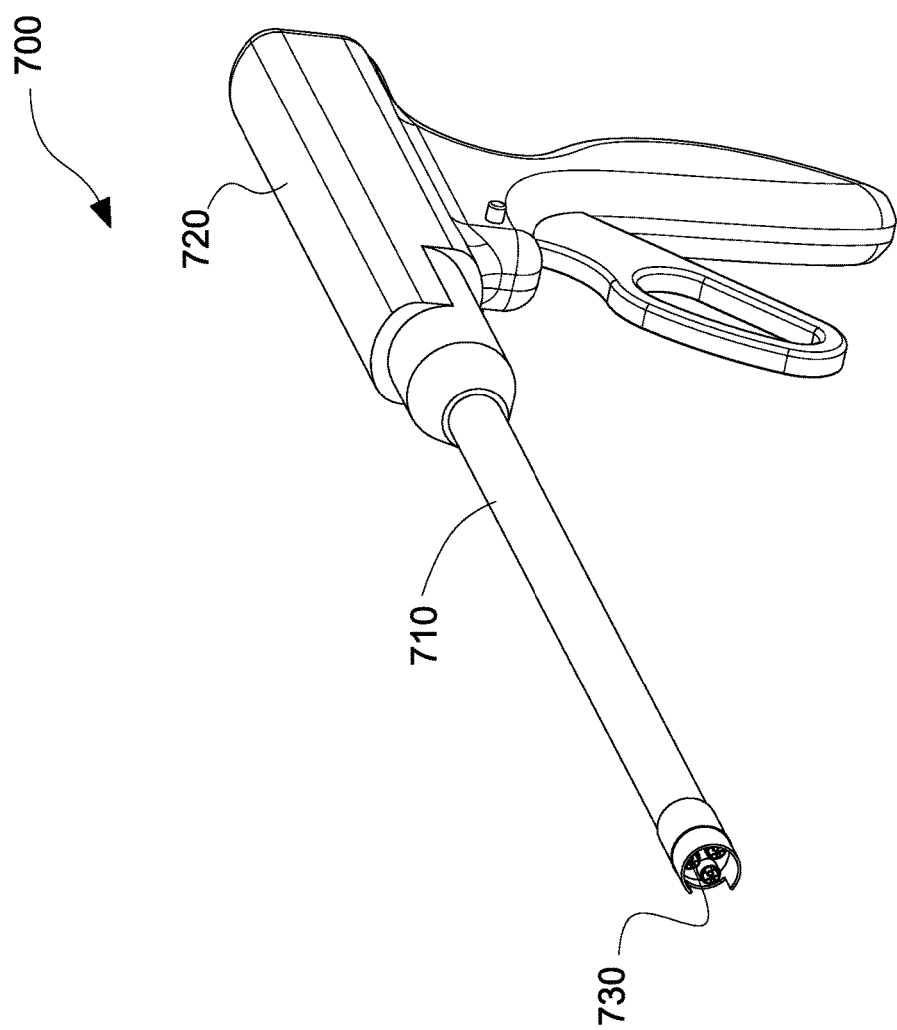
FIG. 7 illustrates a handheld electrospinning device, in accordance with the embodiments of the present disclosure.

With reference to FIG. 7, a handheld electrospinning device is illustrated, in accordance with the embodiments of the present disclosure.

The handheld electrospinning device 700 includes a shaft 710 connected to a handle portion 720 at a proximal end thereof. The shaft 710 also includes an electrospinning device 730 connected at a distal end thereof. The electrospinning device 730 may include the nozzles/needles described with reference to FIGS. 3A-6B. The shaft 710 may be a flexible shaft. The handheld electrospinning device 700 allows a user, such as a surgeon, to control deposition of polymer solution on a substrate or tissue of a patient. The handheld electrospinning device 700 includes a blow-spraying function to achieve various deposition rates of small scale fibers 510, large scale 520, and/or droplets 530 (see FIG. 5).

The diameter of the shaft 710 may be varied for different applications. By using fewer needles and nozzles, a smaller diameter catheter device may be used in endoscopic procedures. For example, the diameter may be between 2.2 mm and 3.3 mm. This may be preferred, for example, when sinus surgery is conducted. By using more needles and nozzles, a larger diameter catheter device may be used in laparoscopic surgeries. For example, the diameter may be between 5 mm and 8 mm. This may be preferred, for example, when hernia repair surgery is conducted.

In FIGS. 6A and 6B, the polymer reservoir may be sourced from a connection to a power supply. However, in FIG. 7, the polymer reservoir may be integral to the surgical instrument. This clearly shown below with reference to FIGS. 8-9B.

Figure 8:
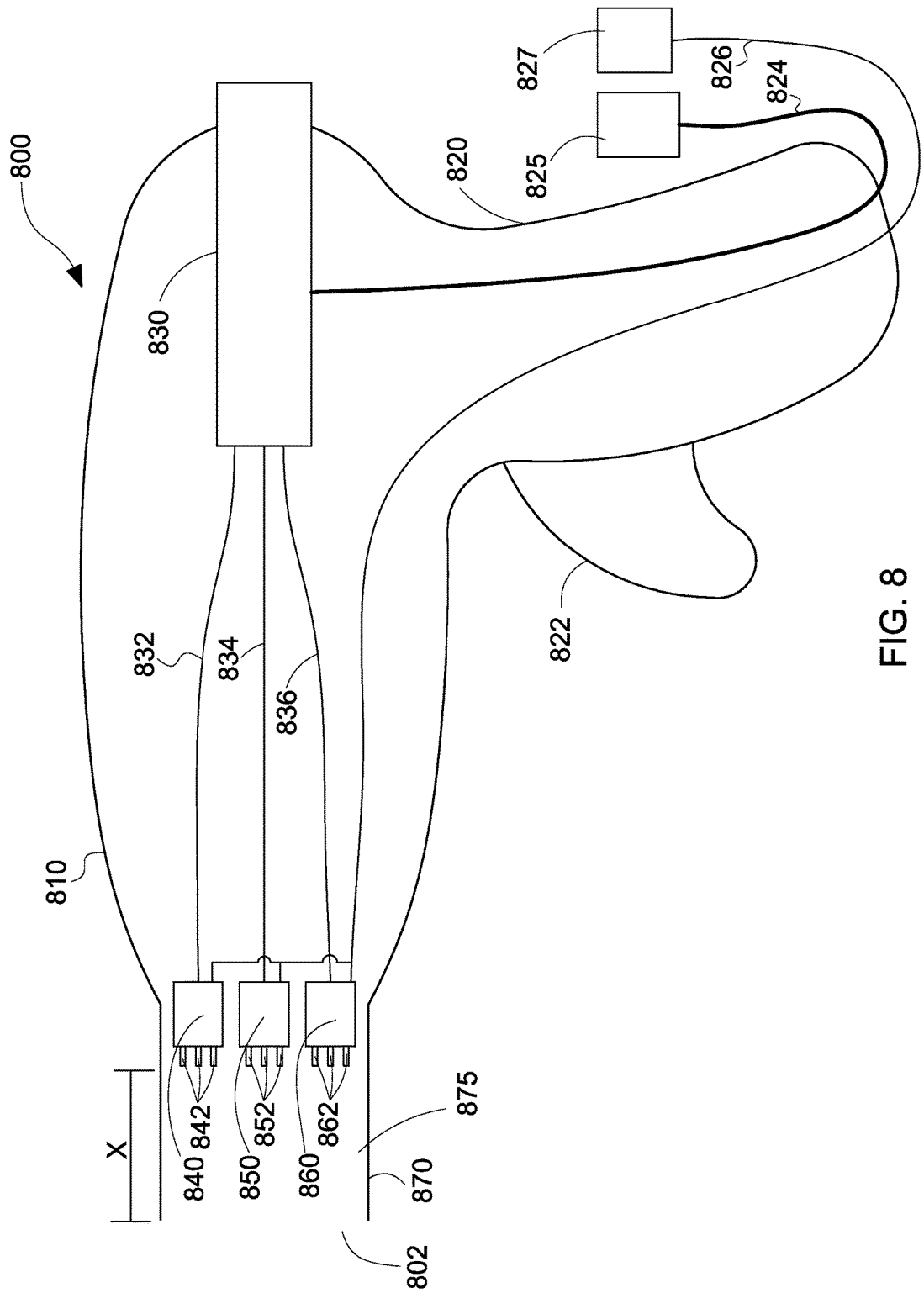
FIG. 8 illustrates a cross-sectional view of a handheld electrospinning device, illustrating the mechanisms for coaxial dispensement of gas and polymer solution, in accordance with the embodiments of the present disclosure.

With reference to FIG. 8, a cross-sectional view of a handheld electrospinning device 800 is depicted, the cross-sectional view illustrating the mechanisms for coaxial dispensement of gas and polymer solution, in accordance with the embodiments of the present disclosure.

The handheld electrospinning device 800 includes a body portion 810 and a handle portion 820. The handle portion 820 includes a trigger mechanism 822. The body portion 810 includes a polymer cartridge 830 connected to compressed gas source 825 via a compressed gas connection 824. The polymer cartridge 830 is connected to a first nozzle 840 via a first cable 832, to a second nozzle 850 via a second cable 834, and a third nozzle 860 via a third cable 836. The nozzles 840, 850, 860 are placed within the shaft portion 870 and are connected to an electrical power source 827 via power connection 826. The first nozzle 840 includes a plurality of needles 842, the second nozzle 850 includes a plurality of second nozzles 852, and the third nozzle 860 includes a plurality of nozzles 862. The plurality of nozzles 840, 850, 860 are positioned or placed or secured a distance "X" away from the distal end 802 of the shaft portion 870. Therefore, a space 875 is provided between the distal end 802 of the shaft portion 870 and the distalmost end of the nozzles 840, 850, 860 having the needles 842, 852, 862. As mentioned above, this space 875 allows for the prevention of arcing.

In operation, the user may trigger the handheld electrospinning device 800 via the trigger mechanism 822 to dispense polymer solution from the needles 842, 852, 862 of nozzles 840, 850, 860, respectively. The polymer solution is shown to be located within a polymer cartridge 830 integrated within the handheld electrospinning device 800. The cartridge 830 may be replaceable or reusable. When the polymer solution is dispensed, air or gas is also automatically dispensed around the needles 842, 852, 862 of the nozzles 840, 850, 860 in order to activate the dual action of electrospinning and spray-blowing.

Figure 9A:
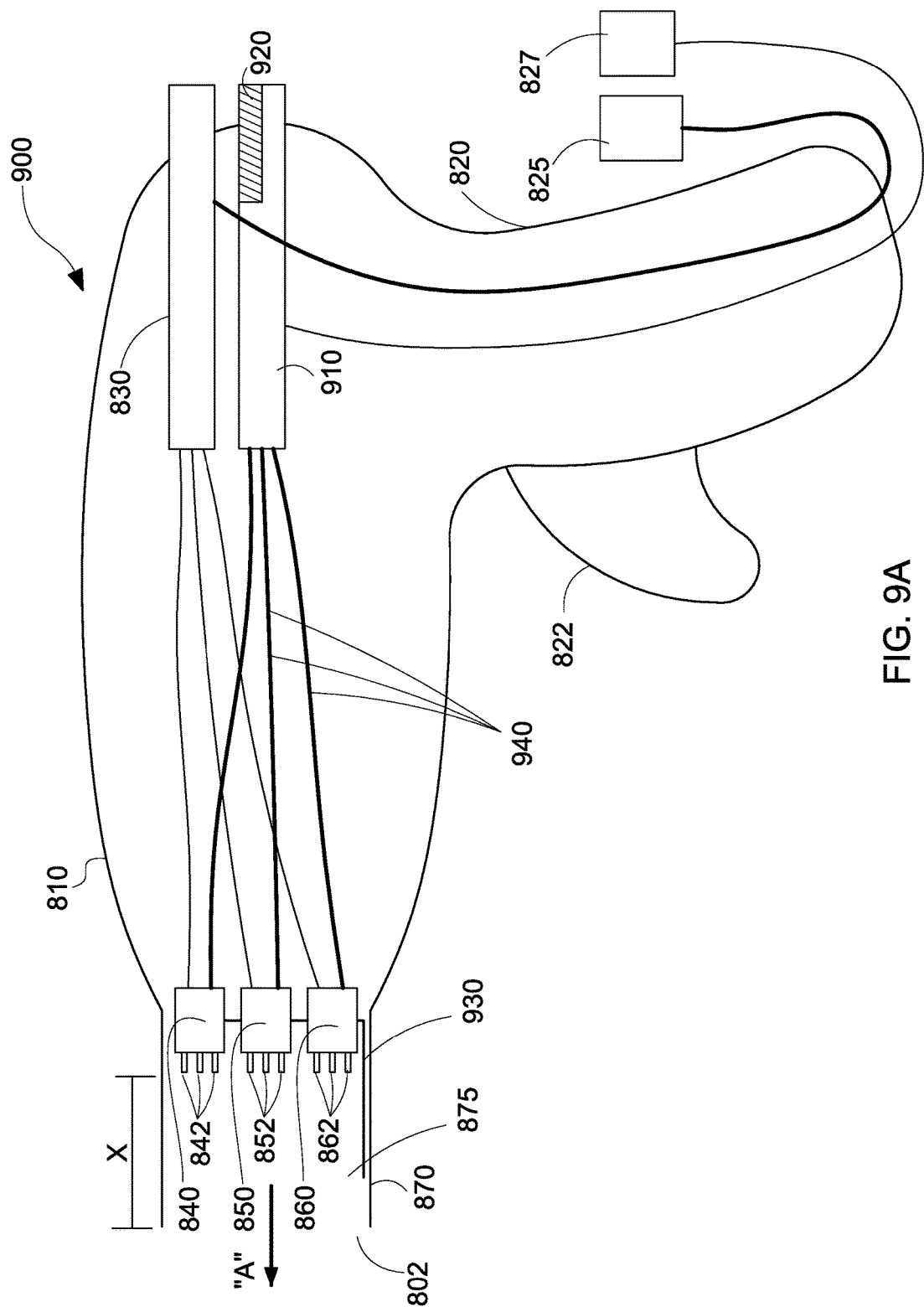
FIGS. 9A and 9B illustrate cross-sectional views of the handheld electrospinning device, illustrating an adjustment mechanism for adjusting positioning of the nozzles during coaxial dispensement of gas and polymer solution, in accordance with the embodiments of the present disclosure.
Figure 9B:
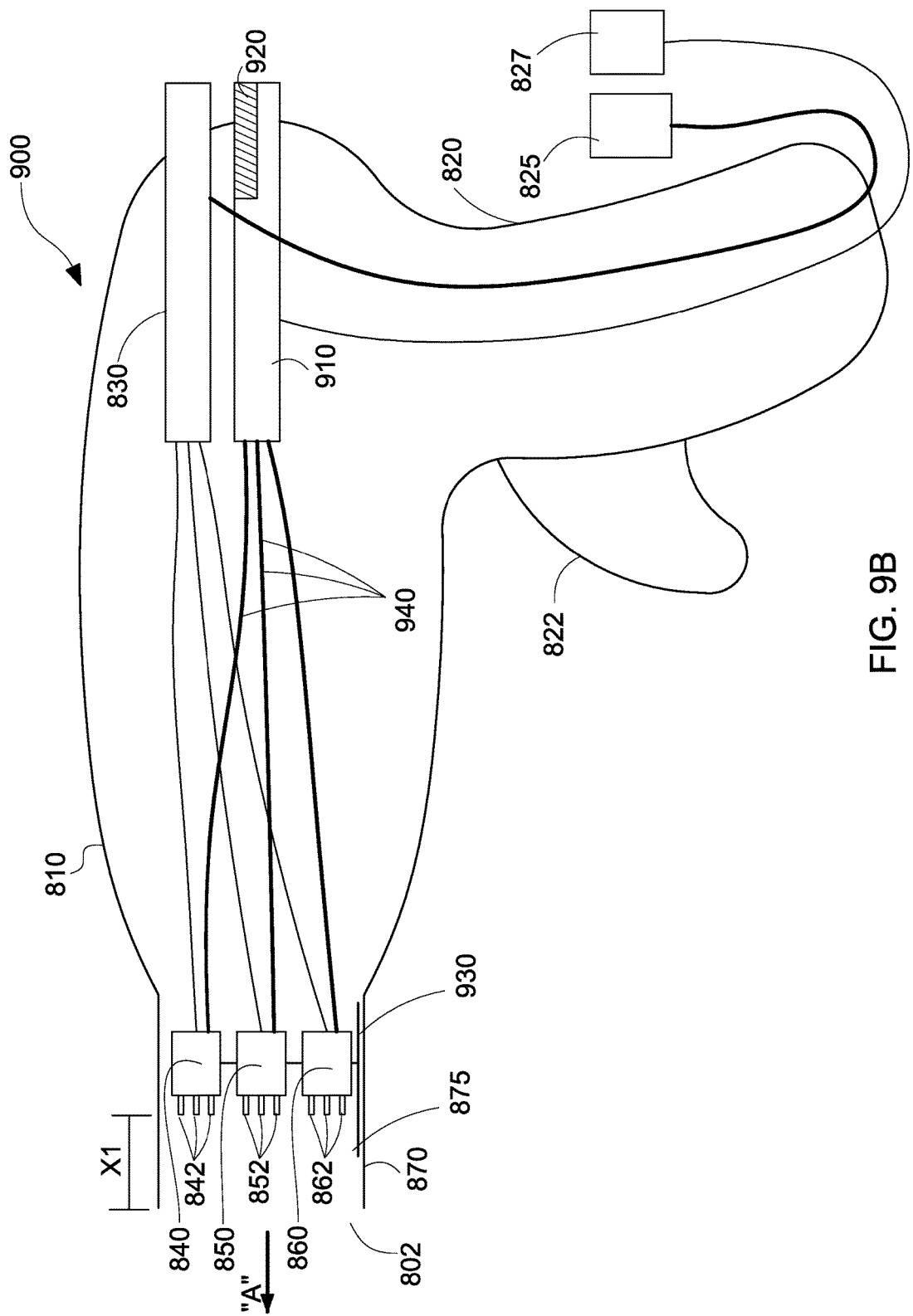

With reference to FIGS. 9A and 9B, cross-sectional views of the handheld electrospinning device 900 are depicted, the cross-sectional view illustrating an adjustment mechanism 910 for adjusting positioning of the nozzles 840, 850, 860 during coaxial dispensement of gas and polymer solution, in accordance with the embodiments of the present disclosure, as previously discussed with regards to the embodiment of FIG. 3A.

FIGS. 9A and 9B illustrate similar elements to FIG. 8, which will not be described in detail for sake of clarity. FIGS. 9A and 9B include an adjustment mechanism 910 having at least one motor 920. The adjustment mechanism 910 allows a user of the handheld electrospinning device 900 to adjust the distance between the nozzles 840, 850, 860 and the distal end 802 of the shaft portion 870. Thus, the plurality of nozzles 840, 850, 860 may be spatially adjusted within the space 875 created within the shaft portion 870. The adjustment mechanism 910 may mechanically cooperate with a retraction mechanism 930. The retraction mechanism 930 may be a guide rail configuration that moves or shifts or displaces the nozzles 840, 850, 860 along a path within the shaft portion 870. Of course, one skilled in the art may contemplate other electromechanical retraction mechanisms for displacing the nozzles 840, 850, 860 within the shaft portion 870 of the handheld electrospinning device 900.

The body portion 810 includes a polymer cartridge 830 connected to compressed gas source 825 via a compressed gas connection 824 (see FIG. 8). The polymer cartridge 830 is connected to a first nozzle 840 via a first cable 832, to a second nozzle 850 via a second cable 834, and a third nozzle 860 via a third cable 836. The nozzles 840, 850, 860 are placed within the shaft portion 870 and are connected to an electrical power source 827 via power connection 826 (see FIG. 8). The gas source 825 supplies compressed gas to the polymer cartridge 830 to force polymer solution 124 (see FIG. 1) through the first, second, and third cables 832, 834, 836, and into the nozzles 840, 850, 860, respectively. The electrical power source 827 provides power to the motor 920 of the adjustment mechanism 910, which in turn activates cables 940 and retraction mechanism 930 to adjust the nozzles 840, 850, 860 within the shaft portion 870.

For example, a user may displace the nozzles 840, 850, 860 from a first position to a second position within the space 875 in order to adjust the deposition rate on a tissue of a patient. The adjustment mechanism 910 allows the nozzles 840, 850, 860 to be horizontally displaced in direction "A" within the shaft portion 870 in order to adjust or vary the distance "X." For example, in FIG. 9B, the user has adjusted the nozzles to distance "X1" from the distal end 802 of the shaft portion 870, where X1 is less than X. In other words, the user moved or shifted or displaced the needles/ nozzles to be closer to the distal end 802. This action may be the result of the surgical procedure to be performed.

For example, if the electrospinning device 900 includes 3 nozzles, the distance may be adjusted between 12 mm to 15 mm to achieve a first deposition rate. However, if the electrospinning device 900 includes 6 nozzles, the distance may be adjusted between 8 mm and 12 mm to achieve that first deposition rate. Further, the user may wish to increase or decrease the deposition rate depending on the type of surgery being performed (e.g., sinus vs. hernia repair). Therefore, the user may adjust or vary or modify the distance of the nozzles from the distal end of the catheter in order to achieve suitable deposition rates. A display (now shown) may be incorporated onto the handheld electrospinning device 900 to display and indicate the distance of the nozzles/needles from the distal end of the shaft or catheter.

In an alternative embodiment, it is contemplated that a user is permitted to selectively open and close nozzles based on the desired deposition rate. For example, if the electrospinning device includes 5 nozzles, each nozzle having 5 needles, the user may selectively turn off or disconnect, temporarily, two of the nozzles since a lower deposition rate may be desired. In other words, the user may decide, based on experience, that 3 nozzles are sufficient to achieve the desired amount of deposition of polymer solution. Therefore, either the body portion 810 or the handle portions 820 may include nozzle shut off switches or buttons to enable the selective opening and closing of nozzles. The user may enable or disable any number of nozzles during any surgical procedure.

It is noted that all the electrospinning systems described with reference to FIGS. 1-9B can be performed by a method including dispensing polymer solution from a reservoir via a dispensing apparatus, connecting a plurality of nozzles to the reservoir, each nozzle of the plurality of nozzles including a plurality of needles, and blowing gas, via a blow-spraying mechanism, around each nozzle of the plurality of nozzles when the polymer solution is dispensed from the plurality of needles.

Figure 10:
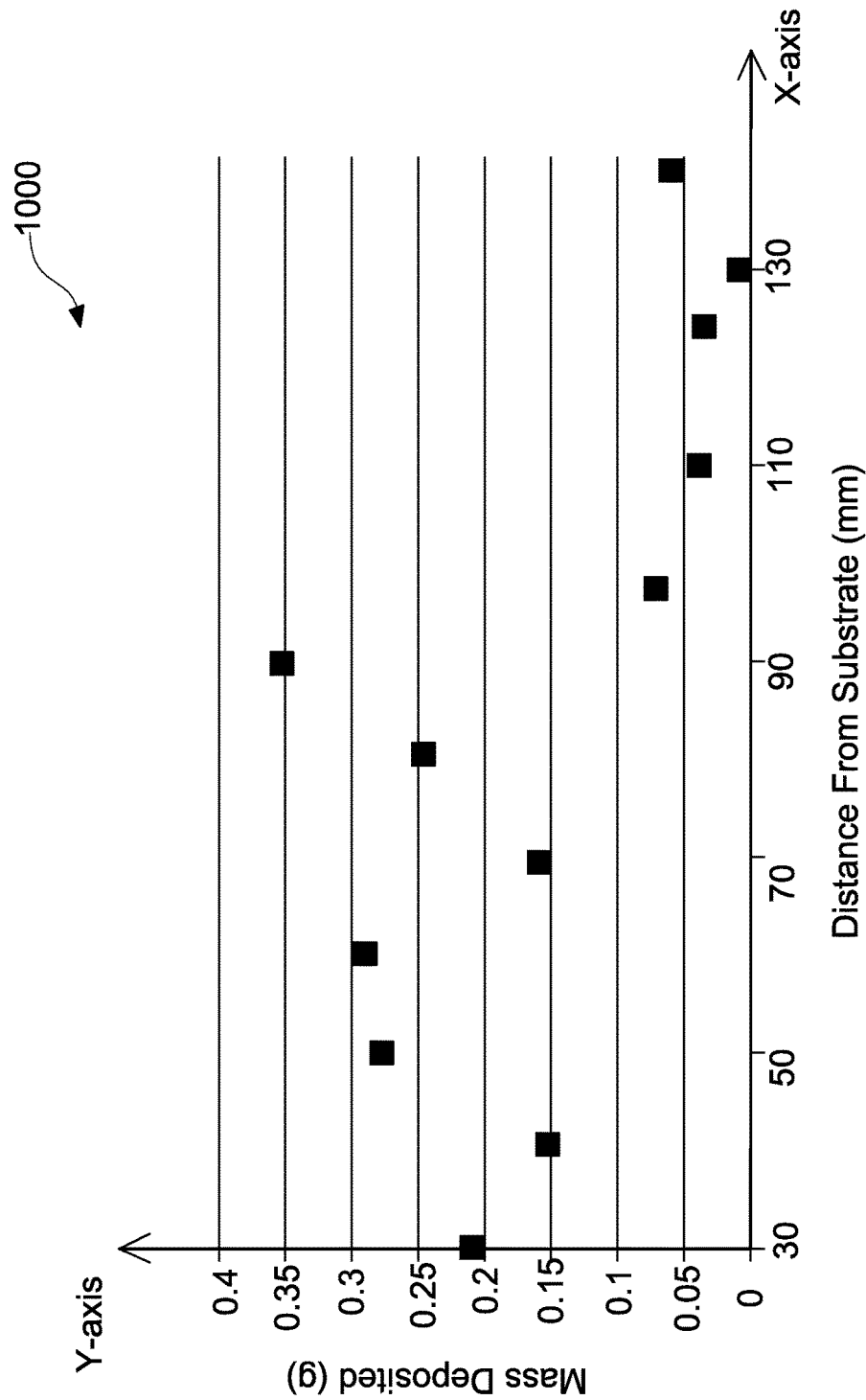
FIG. 10 is a graph depicting mass deposition rates versus distance from a substrate, in accordance with the embodiments of the present disclosure.

With reference to FIG. 10, a graph 1000 depicting mass deposition rates versus distance from a substrate is presented, in accordance with the embodiments of the present disclosure.

The graph 1000 illustrates mass deposited as a function of distance. The y-axis depicts the amount of mass deposited on a substrate, whereas the x-axis depicts the distance of the nozzles from the substrate. For example, when the nozzles are 30 mm away from the substrate, the amount of mass dispensed from the nozzles and deposited on the substrate is approximately 0.2 grams. When the nozzles are 90 mm away from the substrate, the amount of mass dispensed from the nozzles and deposited on the substrate is approximately 0.35 grams. As seen in FIG. 10, for distances between 30 mm and 90 mm, a relatively constant deposition rate of 0.25 g takes place. This occurs when the nozzles are turned on for a period of approximately 30 seconds. However, for distances beyond 90 mm, a relatively small amount of mass is deposited on the substrate. In general, the deposition rate varies linearly with both time and number of nozzles. Additionally, the ratio of nozzles to needles controls the balance between large diameter fibers and small diameter fibers. Therefore, the deposition rate could vary based on the number of nozzles used. The more nozzles used, the higher the deposition rate. However, such deposition rates can also vary based on the distance of the nozzles from the substrate or tissue of the patient.

In summary, using electrospinning of a biodegradable polymer solution allows for a less invasive procedure to repair hernias and chronic wounds. A polymer material can be deposited onto an injury, eventually degrading once the wound has naturally healed. Current sutures and meshes are dependent upon components that are capable of inducing a foreign body reaction and potentially requiring further surgery and repair of the site, due to potential infections or product recalls, whereas an electrospun solution would only degrade into the body. Electrospun polymers also have fiber diameters which are extremely effective as scaffolds for natural tissue regrowth.

Further in summary, the exemplary embodiments of the present disclosure present a device for electrospinning polymer, with the following specific features used in the operation of the handheld electrospinning device. The first feature relates to operating the handheld electrospinning device at a low voltage. For example, by operating the handheld electrospinning device in the 3 kV range, the device complies with various regulatory standards presently applicable to electrosurgery and leverages existing knowledge about electrosurgical power supply design. Low voltage mitigates shock hazards to the extent that it is easier to mitigate shock risk for lower voltages. The second feature relates to coaxial blow-spinning. For example, in order to increase polymer deposition rates to clinically-relevant levels (i.e., deposit mass at a sufficiently quick rate for in situ usage), blow-spraying is combined with standard electrospinning in a coaxial configuration (i.e., compressed gas is blown over the electrospinning needle). Electrospinning, alone, deposits nano-scale fibers (which are desirable because they are highly conducive to cellular infiltration and tissue regrowth), but does so at a very slow rate. Blow-spraying, alone, generates larger fibers (which are much less effective as scaffolds) and the fibers are not electrically-attracted to the substrate (in the way electrospun fibers are), but deposits at a faster rate. Combining blow-spraying with electrospinning provides an apparatus that deposits a mix of nano-scale and larger-scale fibers, enjoys electrical attraction of the fibers to the substrate, and deposits fiber at a fast rate. The third feature relates to using a multi-needle construction or configuration for the handheld electrospinning device. Use of multiple, parallel, coaxial electrospinning nozzles further increases deposition rate and allows varying the ratio of nano-scale to larger-scale fibers. The fourth feature relates to operating the handheld electrospinning device in the far-field regime at voltages at or under 3 kV. Use of the coaxial blow-spinning element allows nano-fiber deposition in the range of a far-field apparatus while employing near-field voltages (which would typically require higher voltage, which is undesirable in this application). The fifth feature relates to in situ deposition of the polymer solution ejected from the multi-nozzle configuration of the handheld electrospinning device. In particular, combination of the above features allows in situ deposition for repair of chronic wounds or hernia defects.

Therefore, the exemplary embodiments of the present disclosure present a handheld electrospinning device that uses coaxial, low-voltage electrospinning to overcome the hurdles in using conventional electrospinning methods. The handheld electrospinning device allows for a method of direct deposition of polymer in vivo and in situ. The handheld electrospinning device is capable of low-voltage far-field (LVFF) electrospinning, which overcomes the potential of arcing while using low-voltage near-field (LVNF) electrospinning. Additionally, large amounts of polymer may be deposited by means of using air blown coaxial electrospinning.

While various embodiments of the present disclosure have been shown and described herein, it will be obvious to those skilled in the art that these embodiments are provided by way of example only. Numerous variations, changes, and substitutions will now occur to those skilled in the art without departing from the present disclosure. Accordingly, it is intended that the invention be limited only by the spirit and scope of the appended claims.

The invention claimed is:

1. An electrosurgical electrospinning device, comprising:
a reservoir having a polymer solution disposed therein, the reservoir cooperating with a dispensing apparatus configured to dispense the polymer solution from the reservoir;
a plurality of nozzles connected to the reservoir, each nozzle of the plurality of nozzles including a plurality of needles; and
a blow-spraying mechanism for blowing gas around each nozzle of the plurality of nozzles when the polymer solution is dispensed from the plurality of needles;
wherein the blow-spraying mechanism and the plurality of nozzles are configured to coaxially apply the gas from the blow-spraying mechanism and the polymer solution from the plurality of needles directly onto tissue at voltages of less than or equal to 3 kV.

2. The electrosurgical electrospinning device according to claim 1, wherein the electrosurgical electrospinning device includes a flexible catheter connected to a body portion, the flexible catheter including the plurality of nozzles therein.

3. The electrosurgical electrospinning device according to claim 2, wherein the flexible catheter includes a proximal end and a distal end, and wherein the plurality of nozzles are positioned a predetermined distance away from the distal end of the flexible catheter, thus defining a space between the distal end of the catheter and the plurality of nozzles.

4. The electrosurgical electrospinning device according to claim 3, wherein the predetermined distance is approximately 8 mm to 15 mm.

5. The electrosurgical electrospinning device according to claim 3, wherein the plurality of nozzles are configured to be repositioned within the flexible catheter to adjust a distance between the plurality of nozzles and a distal end of the flexible catheter.

6. The electrosurgical electrospinning device according to claim 5, wherein the distance adjustment is approximately between 8 mm and 15 mm.

7. The electrosurgical electrospinning device according to claim 1, wherein the plurality of needles is configured to deposit a mixture of nano-scale and large-scale fibers onto tissue.

8. The electrosurgical electrospinning device according to claim 7, wherein a deposition distance of the nano-scale and large-scale fibers is approximately between 25 mm and 100 mm.

9. The electrosurgical electrospinning device according to claim 1, wherein the plurality of nozzles are arranged in a linear configuration.

10. The electrosurgical electrospinning device according to claim 1, wherein the plurality of nozzles are arranged in a circular configuration.

11. The electrosurgical electrospinning device according to claim 1, wherein the plurality of nozzles are arranged as an array.

12. The electrosurgical electrospinning device according to claim 1, wherein the electrospinning device operates at a voltage approximately between 2 kV and 2.98 kV.

13. The electrosurgical electrospinning device according to claim 1, wherein the electrosurgical electrospinning device is a handheld device.

14. The electrosurgical electrospinning device according to claim 1, wherein the electrosurgical electrospinning device is a handheld device including a shaft connected to a handle portion at a proximal end thereof, the shaft incorporating the electrosurgical electrospinning device at a distal end thereof.

15. The electrosurgical electrospinning device according to claim 1, wherein a select number of nozzles of the plurality of nozzles and a select number of needles of the plurality of needles are deactivated during one or more surgical procedures.

16. The electrosurgical electrospinning device according to claim 1, wherein electrospinning occurs in a far field regime.

17. An electro surgical electrospinning method performed by an electrosurgical electrospinning device, the method comprising:
dispensing polymer solution from a reservoir via a dispensing apparatus;
connecting a plurality of nozzles to the reservoir, each nozzle of the plurality of nozzles including a plurality of needles;
blowing gas, via a blow-spraying mechanism, around each nozzle of the plurality of nozzles when the polymer solution is dispensed from the plurality of needles; and
coaxially applying the gas from the blow-spraying mechanism and the polymer solution from the plurality of needles directly onto tissue at voltages of less than or equal to 3 kV.

18. The method according to claim 17, wherein the electrosurgical electrospinning device is a handheld device including a shaft connected to a handle portion at a proximal end thereof, the shaft incorporating the electrosurgical electrospinning device at a distal end thereof.

19. The method according to claim 17, further comprising operating the electrosurgical electrospinning device at a voltage approximately between 2 kV and 2.98 kV.

20. The method according to claim 17, further comprising depositing nano-scale and large-scale fibers onto tissue from a distance of approximately between 25 mm and 100 mm.

* * * * *